(12) United States Patent
Seielstad et al.

(10) Patent No.: US 6,613,346 B2
(45) Date of Patent: *Sep. 2, 2003

(54) CHEWABLE PRODUCT INCLUDING ACTIVE INGREDIENT

(75) Inventors: Donald Seielstad, Frankfort, IL (US);
Henry Tyrpin, Palos Park, IL (US);
Kevin Broderick, Berwyn, IL (US);
James Maxwell, Chicago, IL (US);
David Record, River Forest, IL (US)

(73) Assignee: Wm. Wrigley, Jr. Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/681,935

(22) Filed: Jun. 28, 2001

(65) Prior Publication Data

US 2003/0021830 A1 Jan. 30, 2003

(51) Int. Cl.⁷ .............................................. A61K 47/00
(52) U.S. Cl. .................. 424/439; 424/400; 424/440; 424/441; 424/464; 424/465; 424/474; 424/489; 424/490
(58) Field of Search ................. 424/400, 439, 424/440, 464, 465, 48, 441, 474, 489, 490; 426/5

(56) References Cited

U.S. PATENT DOCUMENTS

| 4,250,195 | A | | 2/1981 | Cherukuri et al. |
|---|---|---|---|---|
| 4,386,106 | A | | 5/1983 | Merritt et al. |
| 4,911,934 | A | * | 3/1990 | Yang et al. ................. 426/302 |
| 5,139,794 | A | | 8/1992 | Patel et al. |
| 5,536,511 | A | * | 7/1996 | Yatka .......................... 426/303 |
| 5,665,406 | A | * | 9/1997 | Reed et al. ..................... 426/5 |
| 6,200,604 | B1 | | 3/2001 | Pather et al. |
| 6,221,402 | B1 | | 4/2001 | Itoh et al. |
| 6,258,376 | B1 | | 7/2001 | Athanikar |
| 6,290,985 | B2 | * | 9/2001 | Ream et al. ................. 424/439 |
| 6,303,159 | B2 | | 10/2001 | Barkalow et al. |
| 6,322,806 | B1 | * | 11/2001 | Ream et al. ................. 424/440 |
| 6,350,480 | B1 | | 2/2002 | Urnezis et al. |
| 6,355,265 | B1 | * | 3/2002 | Ream et al. ................. 424/440 |
| 6,426,090 | B1 | * | 7/2002 | Ream et al. ................. 424/440 |
| 2001/0021403 | A1 | * | 9/2001 | Zyck et al. ..................... 426/3 |
| 2001/0036445 | A1 | | 11/2001 | Anthanikar |
| 2002/0012633 | A1 | | 1/2002 | Gmunder et al. |
| 2002/0022057 | A1 | | 2/2002 | Battery et al. |
| 2002/0039560 | A1 | * | 4/2002 | Ream et al. ................... 424/48 |

FOREIGN PATENT DOCUMENTS

| IT | 01293655 | 7/1997 |
|---|---|---|
| WO | WO 99/27798 | 6/1999 |
| WO | 02/13781 | 2/2002 |

OTHER PUBLICATIONS

Beckett, A.H., et al.; "Buccal absorption of basic drugs and its application as an in vivo model of passive drug transfer through lipid membranes" (1967) *J. Pharm. Pharmac.*, 19 Suppl. 31S–41S.

Weinberg, David. S., et al.; "Sublingal absorption of selected opioid analgesics" (1988) *Clin. Pharmacol Ther.*, 44: 335–342.

U.S. patent application Ser. No. 09/956,445, Gmunder et al., filed Sep. 19, 2001.

U.S. patent application Ser. No. 09/747,323, Zyck et al., filed Dec. 22, 2000.

U.S. patent application Ser. No. 09/924,914, Ream et al., filed Aug. 8, 2001.

* cited by examiner

Primary Examiner—Thurman K. Page
Assistant Examiner—Charesse Evans
(74) Attorney, Agent, or Firm—Bell, Boyd & Lloyd LLC

(57) ABSTRACT

Products and methods of delivering medicaments are provided. The product includes a chewing gum center including a compressible powder that is compressed around the center. The powder includes a medicament that may or may not be encapsulated.

32 Claims, 1 Drawing Sheet

CHEWABLE PRODUCT INCLUDING ACTIVE INGREDIENT

BACKGROUND OF THE INVENTION

The present invention generally relates to the delivery of medicaments and agents. More specifically, the present invention relates to the delivery of medicaments and agents using products including chewing gum.

It is of course known to provide agents to individuals for a variety of purposes. These agents can be used to treat diseases and as such are typically referred to as drugs or medicaments. Likewise, the drugs or medicaments can be used for prophylactic purposes. Still, it is known to provide agents to an individual for a variety of nonmedical purposes including enhancing performance or maintaining or initiating alertness.

There are a great variety of such agents. These agents run the gamut from stimulants such as caffeine to drugs such as analgesics, tranquilizers, cardiovascular products, insulin, etc. Some such agents are taken on an as needed basis while other agents must be taken at regular intervals by the individual.

Typically, drugs (medicaments) are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Except when given intravenously, a drug must traverse several semipermeable cell membranes before reaching general circulation. These membranes act as a biological barrier that inhibits the passage of drug molecules. There are believed to be four processes by which drugs move across a biological barrier: passive diffusion; facilitated diffusion; active transport; and pinocytosis.

Passive diffusion is the transport across the cell membrane wherein the driving force for the movement is the concentration gradient of the solute. In orally administered drugs, this absorption occurs in the small intestines. Facilitated diffusion is believed to be based on a carrier component that combines reversibly with the substrate molecule at the cell membrane exterior. The carrier substrate complex diffuses rapidly across the membrane with release of the substrate at the interior surface. Active transport requires an energy expenditure by the cell and appears to be limited to agents with structural similarities to normal body constituents. These agents are usually absorbed from specific sites in the small intestines. Pinocytosis refers to the engulfing of particulars or fluid by a cell. It is believed to play a minor role in drug transport. *Merck Manual*, 16th Edition, pp. 2598–2599.

In determining the efficacy of a drug and the effectiveness of the use of a drug to treat a disease, drug absorption is a critical concern. Drug absorption refers to the process of drug movement from the site of administration toward the systemic circulation.

Oral administration of drugs is by far the most common method. When administered orally, drug absorption usually occurs due to the transport of cells across the membranes of the epithelial cells within the gastrointestinal tract. Absorption after oral administration is confounded by numerous factors. These factors include differences down the alimentary canal in: the luminal pH; surface area per luminal volume; perfusion of tissue, bile, and mucus flow; and the epithelial membranes. See *Merck Manual* page 2599.

A further issue effecting the absorption of orally administered drugs is the form of the drug. Most orally administered drugs are in the form of tablets or capsules. This is primarily for convenience, economy, stability, and patient acceptance. Accordingly, these capsules or tablets must be disintegrated or dissolved in the stomach before absorption can occur. There are a variety of factors capable of varying or retarding disintegration of solid dosage forms. Further, there are a variety of factors that effect the dissolution rate and therefore determine the availability of the drug for absorption. See *Merck Manual* at page 2600.

Parenteral administration allows for the direct placement of the drug into the blood stream. This usually ensures complete delivery of the dose to the general circulation. However, administration by a route that requires drug transfer through one or more biologic membranes to reach the blood stream precludes a guarantee that all of the drug will eventually be absorbed. Even with parental administration, because capillaries tend to be highly porous, the perfusion (blood flow/gram of tissue) is a major factor in the rate of absorption. Thus, the injection site can markedly influence a drugs' absorption rate; e.g., the absorption rate of diazepam injected IM into a site with poor blood flow can be much slower than following an oral dose. See *Merck Manual* at page 2601.

Not only is drug absorption an issue in drug delivery but, the bioavailability of the drug is also critical. Bioavailability is defined as the rate at which and the extent to which the active moiety (drug or metabolite) enters the general circulation, thereby gaining access to the site of action. Bioavailability depends upon a number of factors, including how a drug product is designed and manufactured, its physicochemical properties, and factors that relate to the physiology and pathology of the patient. See *Merck Manual* at page 2602.

When a drug rapidly dissolves from a drug product and readily passes across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailability owing to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically, parenteral administration requires the use of medical personnel and is just not warranted nor practical for the administration of most agents and drugs, e.g., analgesics. Even when required parenteral administration is not preferred due to patient concerns including comfort, infection, etc., as well as the equipment and costs involved. However, despite best efforts certain therapies require parenterally injected drugs. For example, research for decades has focused on an attempt to deliver insulin to an individual through a non-parental means. Despite such efforts today insulin is still only administered intravenously.

There is therefore a need for an improved method of delivering drugs and agents to an individual.

SUMMARY OF THE INVENTION

The present invention provides improved products and methods for delivering a medicament or agent to an individual. Improved formulations including medicaments or agents are also provided by the present invention.

To this end, the present invention provides a chewing gum product including a medicament comprising a chewing gum center and a compressible composition including a medicament, that may be encapsulated, that is compressed around the chewing gum center.

In an embodiment, the product has a disk shape.

In an embodiment, the product has a pellet shape.

In an embodiment, the product has a spherical shape.

In an embodiment, the product has a cube shape.

In an embodiment, the encapsulated medicament is encapsulated with a composition selected from the group consisting of: natural polymers; synthetic polymers; modified cellulosics; and protein.

In an embodiment, the chewing gum center has the same shape as the product.

In an embodiment, the medicament is selected from the group consisting of: analgesics; muscle relaxants; antacids; antihistamines; decongestants; anti-inflammatories; antibiotics; anti-virals; psycotherapeutic agents; hormones; cardiovascular agents; vitamins; minerals; and nutriceuticals.

In an embodiment, the compressible composition includes a masking agent.

In another embodiment of the present invention, a composition including a medicament is provided comprising a chewing gum center and a compressible formulation including a medicament that surrounds the entire chewing gum center.

In an embodiment, the medicament is encapsulated.

In an embodiment, the medicament is encapsulated with a composition selected from the group consisting of: natural polymers; synthetic polymers; modified cellulosics; and protein.

In an embodiment, the medicament is selected from the group consisting of: analgesics; muscle relaxants; antacids; antihistamines; decongestants; anti-inflammatories; antibiotics; anti-virals; psycotherapeutic agents; hormones; cardiovascular agents; vitamins; minerals; and nutriceuticals.

In a further embodiment of the present invention, an acetominophen containing product is provided comprising a chewing gum center and a compressible composition including encapsulated acetaminophen that is compressed around the chewing gum center.

In yet another embodiment of the present invention a method of delivering a medicament is provided comprising the steps of: providing a chewing gum center; compressing around the chewing gum center a composition including a medicament; and causing an individual in need of the medicament to chew the product.

In an embodiment, the medicament is encapsulated.

In an embodiment, the medicament is selected from the group consisting of: analgesics; muscle relaxants; antacids; antihistamines; decongestants; anti-inflammatories; antibiotics; anti-virals; psycotherapeutic agents; hormones; cardiovascular agents; vitamins; minerals; and nutriceuticals.

Still further, in an embodiment, the present invention provides a method for providing a medicament comprising the steps of: providing a chewing gum center; and compressing around the chewing gum center a composition including a medicament.

Additionally, the present invention provides a method of producing a medicament containing product comprising the steps of: producing a chewing gum center; and surrounding the chewing gum center with a powder that includes a medicament.

Accordingly, an advantage of the present invention is to provide new methods for delivering medicaments to an individual.

Furthermore, an advantage of the present invention is to provide improved products containing a medicament.

Still further, an advantage of the present invention is to provide a method of delivering medicaments to an individual that provides for increase absorption and bioavailability as compared to medicaments that are designed to be absorbed in the GI tract.

Another advantage of the present invention is to provide a novel method of delivering medicaments to an individual that provide relief from pain symptoms.

Further, an advantage of the present invention is to provide chewing gum products containing medicaments that have excellent content uniformity.

Still, an advantage of the present invention is to provide a method of delivering medicaments that does not require the individual to take water.

Moreover, an advantage of the present invention is to provide a method for administering medicaments to an individual that heretofore were administered parentally.

Additionally, an advantage of the present invention is to provide a method for administering medicaments that is more palatable than current methods.

Another advantage of the present invention is to provide an improved method for drug delivery.

An additional advantage of the present invention is that it can provide an acetaminophen containing product that can be chewed and is palatable.

Further, an advantage of the present invention is that a chewing gum product including medicament is provided that can have a variety of shapes.

Additional features and advantages of the present invention will be described in and apparent from the detailed description of the invention and the figures.

DETAILED DESCRIPTION OF THE INVENTION

The present invention provides improved methods for delivering medicaments and other agents to an individual as well as improved products including such medicaments or agents.

Pursuant to the present invention, a medicament is contained in a compressible formulation that surrounds a gum center. As the chewing gum is chewed, the medicament is released into the saliva. During continual chewing, the medicament in the saliva is then forced through the oral mucosa in the buccal cavity due to the pressure created by the chewing. The oral mucosa has a thin epithelium and a rich vascularity. Thus, the oral mucosa favors drug absorption. In contrast to a typically orally ingested drug, wherein the solution is in contact too briefly for absorption to be appreciable through the oral mucosa, it is believed that during chewing, the agent and/or medicament remains in the buccal cavity and is forced through the oral mucosa. Also it has been surprisingly found that an increase in the absorption of the drug is achieved as well as an increase in the bioavailability of the drug as compared to typical oral administration. It has been found that the medicament is absorbed much quicker than if it was swallowed as in a typical oral administration. Indeed, the absorption may in certain cases approach that of a parenteral administration, and the bioavailability is much greater than oral administration.

Figure 1:
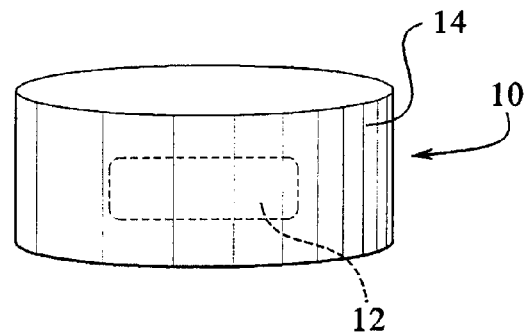
FIG. 1 illustrates generally an embodiment of the product of the present invention.

Referring to FIG. 1, an embodiment of the product 10 of the present invention is illustrated. As illustrated, the product 10 includes a gum center 12. The gum center 12 can be any chewing gum formulation known in the art. Pursuant to the present invention, surrounding the gum center 12 is a compressed powder 14. The compressed powder 14 is a compressible formulation that is compressed around the chewing gum center 12, and includes a medicament or other active agent. It should be noted, if desired, the gum center can also include medicaments.

By using a compressible formulation including a medicament, a variety of shapes and products can be provided. In the preferred embodiment illustrated in FIG. 1, a disk shaped product 10 is provided. However, any geometry can be created, including cubes, pellets, ovals, and spheres. Further, if desired, indicia can be stamped onto the compressed powder 14 and thereby the product 10.

It should be noted that the gum center 12 can either be completely encased by the compressed powder 14 or it may be partially exposed. Further, the gum center 12 may either have the same shape as the compressed powder 14 and the product 10 or it can have a different shape. For example, a spherical gum center can be utilized with an oval compressed product.

Pursuant to the present invention, a compressible formulation, powder, is compressed around the chewing gum center in order to form the product. This provides advantages over creating chewing gum products that may be coated with a medicament. In this regard, typically chewing gum coatings are created by a pan coating process. The present invention provides a number of advantages over the pan coating processes. Pan coating processes typically allow for less than 200 mg/piece of the active agent. There can also be processing control and dosing issues with respect to products produced using current pan coating processes. Further, pan coated procedures may create stability and shelf life issues with respect to the resultant product.

By utilizing a compressible powder for creating a tableted product, excellent content uniformity can be provided. For example, in an embodiment, it has been found that a product can be provided that will have ±3.1% at 300 mg dosage which is ±10.9 mgs.

As noted above, the compressible powder includes a medicament. The medicament can be blended with a powder to create the compressed powder through a variety of methods. The blending may be performed by a standard mixing means, using a Vee Blender, a Ribbon Blender or other mixer. The powder is formulated to provide a compressible matrix, using bulk fillers, sorbitols, sugars, polyols, starches, sugars modified with starches and the like. Preferably, this filler can range from approximately 10 to about 95% by weight composition of the powder and active/medicament blend. Preferably the active/medicament may range from approximately 0.001 to about 60% by weight of the powder and active/medicament blend. Other components that can be present in the powder include flavors, colors, sweeteners and high potency sweeteners. Other excipients can also be used in the powder that are useful in modifying mouthfeel and organoleptic properties of the product. Excipients may also be used to modify dissolution and disintegration properties and binding of the product. Preferably the weight of the powder and active/medicament blend may range from approximately 10 to about 90% weight of the total product.

As noted above, if desired, the medicament can be encapsulated or it can be free. In order to produce the encapsulated medicament, a variety of technologies can be utilized. For example, film coating technologies can be used to provide effective taste masking of a pharmaceutical agent. A number of materials can be utilized to encapsulate the medicament including, natural polymers, synthetic polymers, modified cellulose, waxes, fats, oils, and proteins. In addition, a diverse range of modifiers can be used, including, but not limited to, plasticizers, pore formers, disintegrants, waxes, lipids, fats, fatty acids, polylactides, solubilizers, and absorption enhancers.

Several encapsulating techniques can be used to encapsulate the medicament. These include fluid-bed coating and its variations, low-shear wet granulations, high-shear wet granulations, and spray dry processes. The encapsulations provide for coated solid particles and matrix dispersions. This enhances bioavailability, taste masking, and tailored release profiles. It has been found that high-shear granulations of active powder with modifying agents provide for taste masking, absorption enhancement, dissolution aides, and mouth feel modifiers. The tailored release profile focuses on the immediate release of a pharmaceutical/active, a standard delivery profile of pill forms of medicaments/actives and delayed or sustained release of a pharmaceutical active as given by entreric coating processes.

The compressed powder can include masking agents. In this regard, high-intensity sweeteners and appropriate flavors can be used to mask any off notes that are present due to the medicament or agent. It has been found that with respect to certain medicaments or agents that may have an astringent or bitter taste that by adding a masking agent to the formulation, that a much more palatable formulation, including the medicament, can be provided.

The masking agents, in an embodiment, are selected from the group consisting of sucralose; zinc gluconate; ethyl maltol; glycine; acesulfame-k; aspartame; saccharin; fructose; xylitol; maltitol; cooling agents; isomalt; salt; spray dried licorice root; glycyrrhizin; dextrose; sodium gluconate; sucrose; glucono delta-lactone; ethyl vanillin; and vanillin.

In an embodiment of the invention, sufficient masking agent will be used in the compressed powder to improve and provide acceptable organoleptic properties to the chewing gum product. As used herein to provide "acceptable organoleptic properties" means that the product will have a sufficiently pleasant, or at least non-offensive taste, to allow the consumer to chew the chewing gum for at least two minutes. Whether a masking agent is necessary and/or the amount of masking agent will vary depending on medicament. Of course, if desired, more than one masking agent can be used, e.g., zinc gluconate and a sweetener or flavor. In an embodiment, the masking agent may comprise approximately 10% to about 90% by weight of the powder formulation.

In a preferred embodiment, the compressed powder includes a high-intensity sweetener such as aspartame, sucralose, and acesulfame-k. In an embodiment, the high-intensity sweetener comprises approximately 0.5% to about 5% by weight of the coating.

The core, center of the product is chewing gum. It has been found that this component of the present invention reduces any aftertaste that may be present from the medicament. The gum also speeds delivery of the drug by increasing production of saliva. The increase in saliva assists in swallowing the medicament without drinking water. Further an increased absorption is achieved through oral mucosa by creating fluid pressure.

Standard gum formulas known in the art can be used for the chewing gum core center of the product. The chewing gum will be formulated in size, mass and texture to minimize chew-in activity of medicament into the cud. This can be accomplished by increasing the amount of base and filler in the chewing gum. The amount of gum will be enough to provide a reasonable cud size, e.g., in a range of 0.1 grams to 3 grams.

The compression of the powder and medicament blend around the chewing gum center can be performed by modifying existing tableting equipment presently used in the pharmaceutical industry. For example, a modification can be made to equipment as the Single Layer or Multilayer Rotary Tablet Press, to include placement of a core, prior to final compression. The powder blend will then surround the gum core center and is mechanically compressed to form the final product.

It has also been surprisingly found that by placing a medicament in an powder that is compressed around a gum center less medicament or agent can be placed in the product than is typically orally administered to an individual to achieve an effect and the same bioequivalence can be achieved. In fact, it has been surprisingly found that in certain instances, for at least certain drugs and agents, the administration of the medicament or agent using chewing gum through the buccal cavity can provide an increase effect even as compared to parenteral administration.

It is envisioned, that a variety of different medicaments and agents can be placed in the compressed powder. Generally, such medicaments include, inter alia, analgesics, antibiotics, antivirals, antihistamines, anti-inflammatories, cancer chemotherapies, antimycotics, oral contraceptives, diuretics, antitussives, anesthetics, nutraceuticals, bioengineered pharmaceuticals, oral vaccines, probiotics, decongestants, antacids, muscle relaxants, psychotherapeutic agents, hormones, insulin, vitamins, and minerals and cardiovascular agents. For example, such agents include, inter alia, stimulants such as caffeine. It is envisioned, that depending on the medicament, the resultant chewing gum can be used to treat, inter alia: coughs; colds; motion sickness; allergies; fevers; pain; inflammation; sore throats; cold sores; sinus problems; diarrhea; diabetics; depression; anxiety; and other maladies and symptoms. Specific agents/medicaments include, by way of example and not limitation: caffeine; aspirin; acetaminophen; ibuprofen; hydroxycitric acid; antacids; chromium picolinate; phosphatidylserine; nicotine (for smoking cessation); insulin; Echinacea purpurea; zinc; vitamin C; ginseng; kola nut; kaua kaua; and chamomile.

In an embodiment, the medicaments are contained in the compressed powder coating of the chewing gum formulation at levels of approximately 50 micrograms to 500 milligrams. The specific levels will depend on the active ingredient. The level of medicament or agent in the compressed powder of the chewing gum formulation is selected so as to create, when the product is chewed, a sufficiently high concentration of the medicament or agent in the saliva.

In an embodiment of the present invention, the product includes encapsulated acetaminophen. Preferably the product includes at least 250 mg of acetaminophen and in an embodiment 500 mg. It has been found that the acetaminophen is quickly released from the product into the saliva of the individual chewing the product.

Pursuant to the present invention, depending on the medicament, the dosing regiment will change. For example, if the medicament is an analgesic, the chewing gum would be taken on an as needed basis. Of course, similar to the oral administration of an analgesic, there would be restrictions on the number of pieces of chewing gum, chewed, for example, not more often than one stick every four hours and not more often than four to five times a day.

The powder including medicament can surround a variety of different gum center compositions. Referring now to the chewing gum center, pursuant to the present invention, the gum center may be based on a variety of different chewing gums that are known. For example, the gum center can be low or high moisture, sugar or sugarless, wax containing or wax free, low calorie (via high base or low calorie bulking agents), and/or may contain dental agents.

Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. Typically, gum base comprises approximately 20 to about 40% of the gum product. However, because in the present invention such a high level of coating is used, the gum center is unusually small; otherwise the entire coating chewing gum piece would be too large for consumption. If atypical amount of gum base was used in the small gum center, it would result in an inadequate cud to masticate. Consequently, in the present invention, the base level is higher than normal. The insoluble gum base can constitute approximately 30% to about 90% by weight of the chewing gum, in an embodiment, the gum base comprises at least 50% of the chewing gum.

In an embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate—vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids); and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High-intensity artificial sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

The gum center can be prepared using a variety of different methods and machinery known in the art. For example, the formulation can be mixed using a sigma blade mixer. The center formulation may also be made by continuous processing equipment known in the art. Conventional sheeting and scoring machinery can be used to form and score the centers or the centers can be made on a forming machine that involves a drop frame and nitrogen cooling allowing spheres, ovals, and other shapes to be made.

By way of example, and not limitation, examples of some coated chewing gum formulations including a medicament or agent are as follows:

EXAMPLES

Examples of formulations follow.

Chewing Gum Center Formulation, percentage composition:

| Ingredient | Example 1 | Example 2 | Example 3 | Example 4 | Example 5 |
|---|---|---|---|---|---|
| Sorbitol | 30.70 | 30.70 | 34.80 | 32.30 | 35.50 |
| Base | 44.00 | 46.00 | 41.00 | 44.00 | 38.00 |
| Calcium Carbonate | 10.00 | 9.00 | 10.50 | 10.00 | 11.00 |
| Maltitol | 2.00 | 3.00 | 1.50 | 2.00 | 2.50 |
| Glycerin | 1.50 | 5.00 | 3.50 | 4.00 | 4.50 |
| 70% Sorbitol Solution | 3.50 | 2.50 | 3.50 | 3.50 | 2.00 |
| Flavor | 6.00 | 2.50 | 2.50 | 2.50 | 3.00 |
| Menthol | 0.50 | — | — | 0.50 | 1.00 |
| Granulated Aspartame | — | 0.50 | — | 0.50 | — |
| Encapsulated Aspartame | 0.10 | 0.10 | — | 0.50 | 0.50 |
| Acesulfame K | 1.00 | — | 1.00 | — | 1.00 |
| Encapsulated Sucralose | 0.45 | — | 1.00 | — | 0.30 |
| Citric Acid | — | 0.50 | — | — | 0.40 |
| Lecithin | 0.25 | 0.20 | 0.20 | 0.20 | 0.30 |
| Total Percentage | 100.00 | 100.00 | 100.00 | 100.00 | 100.00 |

Chewing gum ingredients may be mixed in a Sigma Blade Mixer or in a continuous extruding mixer. After mixing, the gum mass is passed through a series of rollers ultimately ending with a pelletizing roller which scored the gum into pieces of the desired mass. Those were manually reformed into disk shaped pieces. A preferred method would be a sheeting method, which would produce the desired disk shaped center without manual manipulation.

Powder Coating Formulation, percentage composition:

| Ingredient | Example 6 | Example 7 | Example 8 | Example 9 | Example 10 |
|---|---|---|---|---|---|
| Sorbitol | 70.90 | — | — | 63.30 | — |
| Dextrose | — | 68.30 | — | — | 60.00 |
| Fructose | — | — | 65.00 | — | — |
| Encapsulated Acetaminophen | 15.00 | — | — | 22.60 | — |
| Powder Acetaminophen | — | 18.00 | — | — | — |
| Granular Acetaminophen | — | — | 20.00 | — | — |
| Granulated Acetaminophen | — | — | — | — | 25.00 |
| Polyvinyl pyrolidone | — | 5.00 | — | — | 6.50 |
| Microcrystalline Cellulose | 6.00 | — | 5.50 | 6.00 | — |
| Aspartame | 3.00 | 2.40 | 2.00 | 2.40 | 5.00 |
| Sucralose | 1.50 | 2.00 | 3.50 | 1.50 | — |
| WS-23 | 0.10 | 0.20 | 0.30 | 0.10 | 0.25 |
| Calcium Stearate | — | 1.00 | — | — | 0.75 |
| Magnesium Stearate | 1.00 | — | 0.60 | 1.00 | — |
| Flavor | 3.00 | 3.00 | 3.00 | 3.00 | 2.20 |
| Color | 0.10 | 0.10 | 0.10 | 0.10 | 0.30 |
| Total Percentage | 100.00 | 100.00 | 100.00 | 100.00 | 100.00 |

The powder formulations can then be placed around the chewing gum centers to make a product. For example, a chewing gum as in Example 4 was coated with Example 9, by using a calibrated volumetric scoop to measure 0.9 grams of powder and poured into the tablet die on a rotary tablet press. The gum center was manually placed on top of the powder and centered, and the volumetric scoop was used to deliver an additional 0.9 gm of coating powder over the gum center. The rotary press was cycled through one full rotation to compress the powder around the gum center.

Experiment No. 1

The aforementioned Example 11 was compared to a pan coated product made in the following manner: Chewing gum ingredients may be mixed in a Sigma Blade Mixer or in a continuous extruding mixer. After mixing, the gum mass is passed through a series of rollers ultimately ending with a pelletizing roller which scored the gum into pieces of the desired shape and size.

The gum centers were loaded into a conventional perforated pan and coated in a manner typical of standard confections. The pellet bed was doused with syrup and allowed to tumble for a period of time to distribute the syrup and dried for another fixed period of time. During the intermediate phases of this process, a dry charge consisting of maltitol and powdered acetaminophen was sprinkled on the moist bed of pellets and incorporated into the pellet coating prior to complete drying. This is repeated as necessary to build up the desired drug dose on the outside of the pellets.

Kinetic analysis was performed on three subjects to determine the amount of acetaminophen, which was chewed into the cud. The comparative examples used were Driam pan coated gum with a 195 mg/pellet of acetaminophen and Driam pan coated gum with 150 mg/pellet of acetaminophen were compared to the experimental samples of Compressed Tablet Chewing Gum with 355 mg/pellet of acetaminophen. The time points taken for the pan coated 195 mg/pellet product were at 0, 2, 5, 10 and 20 minutes. Time points for the 150 mg/pellet product were at 0, 10, 20, 30, and 40 minutes. The time points taken for the Compressed Tablet Chewing Gum 355 mg/pellet product were 0, 1, 3, 5, 8, 14, and 20 minutes.

Figure 2:
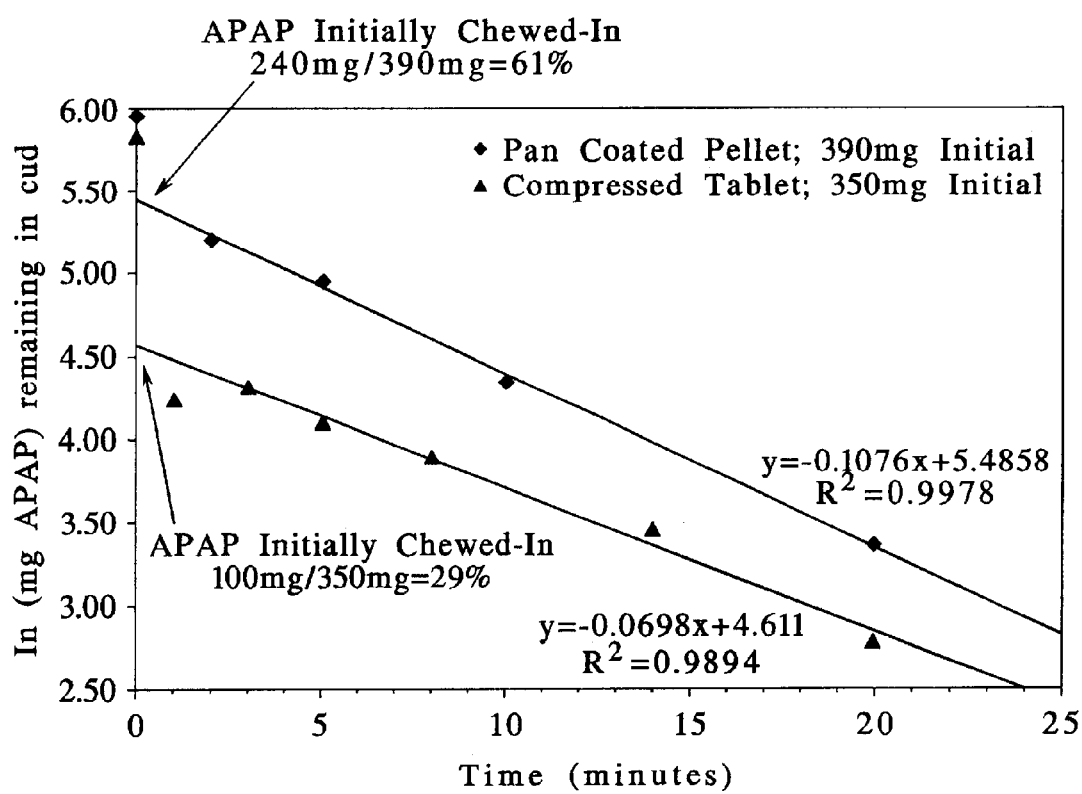
FIG. 2 illustrates graphically the results of Experiment No. 1 that is discussed supra.

FIG. 2 illustrates graphically the results of this analysis.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A chewing gum product including a medicament comprising:

a chewing gum center; and a compressible composition comprising an encapsulated medicament that is compressed around the chewing gum center.

2. The chewing gum product of claim 1 wherein the product has a disk shape.

3. The chewing gum product of claim 1 wherein the product has a pellet shape.

4. The chewing gum product of claim 1 wherein the product has a spherical shape.

5. The chewing gum product of claim 1 wherein the product has a cube shape.

6. The chewing gum product of claim 1 wherein the encapsulated medicament is encapsulated with a composition selected from the group consisting of: natural polymers; synthetic polymers; modified cellulosics; waxes; fats; oils; and protein.

7. The chewing gum product of claim 1 wherein the chewing gum center has the same shape as the product.

8. The chewing gum product of claim 1 wherein the medicament is selected from the group consisting of: analgesics; muscle relaxants; antacids; antihistamines; decongestants; anti-inflammatories; oral vaccines; probiotics; antibiotics; anti-virals; cancer chemotherapies; antimycotics; oral contraceptives; diuretics; antitussives; anesthetics; bioengineered pharmaceuticals; psycotherapeutic agents; hormones; cardiovascular agents; vitamins; insulin; minerals; and nutraceuticals.

9. The chewing gum product of claim 1 wherein the compressible composition includes a masking agent.

10. A composition including a medicament comprising:

a chewing gum center; and a compressible formulation including a medicament that surrounds the entire chewing gum center.

11. The composition of claim 10 wherein the medicament is encapsulated.

12. The composition of claim 10 wherein the chewing gum composition has a disk shape.

13. The composition of claim 10 wherein the medicament is encapsulated with a composition selected from the group consisting of: natural polymers; synthetic polymers; modified cellulosics; waxes; fats; oils; and protein.

14. The composition of claim 10 wherein the medicament is selected from the group consisting of: analgesics; muscle relaxants; antacids; antihistamines; decongestants; anti-inflammatories; antibiotics; anti-virals; oral vaccines; probiotics; psycotherapeutic agents; hormones; cardiovascular agents; vitamins; minerals; insulin; and nutraceuticals.

15. An acetominophen containing product comprising:

a chewing gum center; and a compressible composition including encapsulated acetaminophen that is compressed around the chewing gum center.

16. The acetominophen containing product of claim 15 wherein the product has a disk shape.

17. The acetominophen containing product of claim 15 wherein the acetominophen is encapsulated with a composition selected from the group consisting of: natural polymers; synthetic polymers; modified cellulosics; waxes; fats; oils; and protein.

18. The acetominophen containing product of claim 15 wherein the chewing gum center has the same shape as the product.

19. A method of delivering a medicament comprising the steps of:

providing a chewing gum center;

compressing around the chewing gum center a composition including a medicament to produce a product; and causing an individual in need of the medicament to chew the product.

20. The method of claim 19 wherein the medicament is encapsulated.

21. The method of claim 20 wherein the medicament is encapsulated with a composition selected from the group consisting of: natural polymers; synthetic polymers; modified cellulosics; and protein.

22. The method of claim 19 wherein the product is chewed a plurality of times per day.

23. The method of claim 19 wherein the medicament is selected from the group consisting of: analgesics; muscle relaxants; antacids; antihistamines; decongestants; anti-inflammatories; antibiotics; anti-virals; oral vaccines; probiotics; cancer chemotherapies; antimycotics; oral contraceptives; diuretics; antitussives; anesthetics; bioengineered pharmaceuticals; insulin; psycotherapeutic agents; hormones; cardiovascular agents; vitamins; minerals; and nutraceuticals.

24. The method of claim 19 wherein the medicament is acetominophen.

25. A method for providing a medicament comprising the steps of:

providing a chewing gum center; and compressing around the chewing gum center a composition including a medicament.

26. The method of claim 25 wherein the medicament is encapsulated with a composition selected from the group consisting of: natural polymers; synthetic polymers; modified cellulosics; waxes; fats; oils; and protein.

27. The method of claim 25 wherein the medicament is selected from the group consisting of: analgesics; muscle relaxants; antacids; antihistamines; decongestants; anti-inflammatories; antibiotics; anti-virals; cancer chemotherapies; antimycotics; oral contraceptives; diuretics; antitussives; anesthetics; oral vaccines; probiotics; bioengineered pharmaceuticals; insulin; psycotherapeutic agents; hormones; cardiovascular agents; vitamins; minerals; and nutraceuticals.

28. The method of claims 25 wherein the medicament is acetominophen.

29. A method of producing a medicament containing product comprising the steps of:

producing a chewing gum center; and surrounding the chewing gum center with a compressible powder that includes a medicament.

30. The method of claim 29 wherein the medicament is encapsulated with a composition selected from the group consisting of: natural polymers; synthetic polymers; modified cellulosics; and protein.

31. The method of claim 29 wherein the medicament is selected from the group consisting of: analgesics; muscle relaxants; antacids; antihistamines; decongestants; anti-inflammatories; antibiotics; anti-virals; cancer chemotherapies; antimycotics; oral contraceptives; diuretics; antitussives; anesthetics; bioengineered pharmaceuticals; psycotherapeutic agents; hormones; cardiovascular agents; oral vaccines; probiotics; insulin; vitamins; minerals; and nutraceuticals.

32. The method of claim 29 including the step of compressing the powder around the chewing gum center.

* * * * *